(12) United States Patent
Shi et al.

(10) Patent No.: US 11,900,027 B2
(45) Date of Patent: Feb. 13, 2024

(54) EPIDEMIC FORECASTING MODEL FOR POLICIES OF PREVENTION, CONTROL AND ISOLATION

(71) Applicant: BEIHANG UNIVERSITY, Beijing (CN)

(72) Inventors: Honghao Shi, Beijing (CN); Jingyuan Wang, Beijing (CN)

( * ) Notice: Subject to any disclaimer, the term of this patent is extended or adjusted under 35 U.S.C. 154(b) by 537 days.

(21) Appl. No.: 17/213,375

(22) Filed: Mar. 26, 2021

(65) Prior Publication Data
US 2022/0138373 A1     May 5, 2022

Related U.S. Application Data

(63) Continuation of application No. PCT/CN2020/139719, filed on Dec. 26, 2020.

(51) Int. Cl.
*G06F 30/20*     (2020.01)

(52) U.S. Cl.
CPC ................... *G06F 30/20* (2020.01)

(58) Field of Classification Search
CPC ...................................................... G06F 30/20
See application file for complete search history.

(56) References Cited

U.S. PATENT DOCUMENTS

| 11,056,242 B1 | 7/2021 | Jain et al. |
| 2017/0103072 A1 | 4/2017 | Yuen et al. |
| 2017/0316324 A1 | 11/2017 | Barrett et al. |
| 2020/0373018 A1 | 11/2020 | Segal |

FOREIGN PATENT DOCUMENTS

| CN | 111445997 A | 7/2020 | |
| CN | 111524611 A | 8/2020 | |
| CN | 111863271 A | * 10/2020 | ............ G16H 50/80 |
| CN | 111883260 | 11/2020 | |
| CN | 111883260 A | * 11/2020 | ............ G16H 50/80 |

OTHER PUBLICATIONS

Zou D, Wang L, Xu P, Chen J, Zhang W, Gu Q. Epidemic model guided machine learning for COVID-19 forecasts in the United States. MedRxiv. May 25, 2020:2020-05. (Year: 2020).*

* cited by examiner

*Primary Examiner — Chuen-Meei Gan*

(57) ABSTRACT

An epidemic forecasting model for policies of prevention, control and isolation is disclosed, including: establishing a SUEIR model; dividing, by the SUEIR model, population according to an ability of infection and a way of infection; classifying patients further into three states: unconfirmed, confirmed but not in isolation, and confirmed and in isolation; calculating a number of people in each state in the future by using the SUEIR model; and accumulating the number of people in the confirmed state to realize the forecasting of the number of confirmed cases. The disclosure not only accurately forecasts the number of confirmed cases, but also explains various policies of prevention and control.

1 Claim, 1 Drawing Sheet

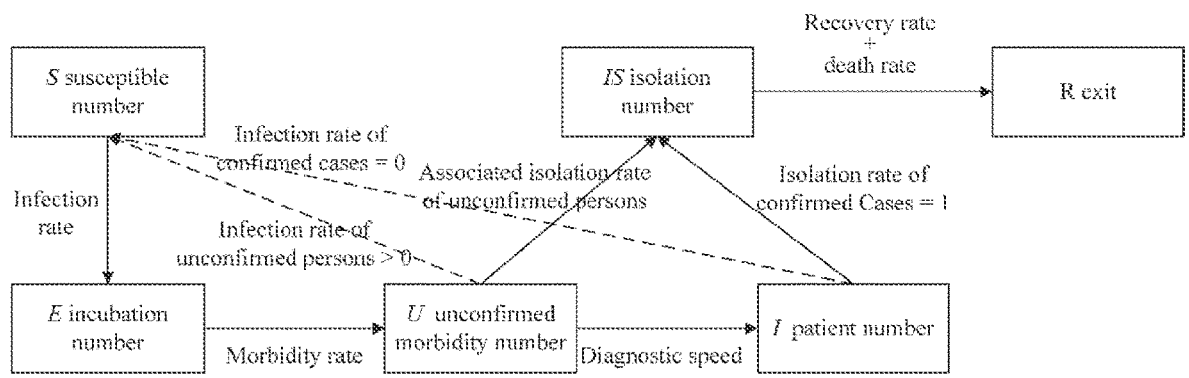

EPIDEMIC FORECASTING MODEL FOR POLICIES OF PREVENTION, CONTROL AND ISOLATION

CROSS-REFERENCE TO RELATED APPLICATIONS

This application is a continuation of International Patent Application No. PCT/CN2020/139719 with a filing date of Dec. 26, 2020, designating the United States, and further claims priority to Chinese Patent Application No. 202011218773.9 with a filing date of Nov. 4, 2020. The content of the aforementioned applications, including any intervening amendments thereto, are incorporated herein by reference.

TECHNICAL FIELD

The present disclosure relates to the field of epidemic forecasting, and more specifically, to an epidemic forecasting model for policies of prevention, control and isolation.

BACKGROUND

Current epidemic forecasting and analysis is often limited to data collection, data sorting and model design optimization, missing a complete product line to screen data, collect data, sort data, design optimization of targeted models, and finally present a customization report.

The existing models for forecasting epidemic development are based on kinetic models that analyze the diseased states of different populations and are not suitable for epidemic forecasting in information age with outside policy implications. Because of the need for immediate forecasting of epidemics, the exact number of infected individuals cannot be obtained at the time of forecasting, and only the number of confirmed individuals can be obtained. The parameters that affect contagion also only have simple rates of contagion, cure, and mortality, and it is impossible to realize the impact of prevention and control policies.

Therefore, how to provide an epidemic forecasting model for policies of prevention, control and isolation is an urgent problem for those skilled in the art.

SUMMARY

In view of the above, the present disclosure is to provide an epidemic forecasting model for policies of prevention, control and isolation. The model accurately forecasts the number of confirmed cases, and explains various policies of prevention and control.

Technical solutions of the present disclosure are specifically described as follows.

An epidemic forecasting model for policies of prevention, control and isolation includes:
establishing a SUEIR model;
dividing, by the SUEIR model, population according to an ability of infection and a way of infection;
classifying patients further into three states: unconfirmed, confirmed but not in isolation, and confirmed and in isolation;
calculating a number of people in each state in the future by using the SUEIR model; and
accumulating the number of people in the confirmed state to realize the forecasting of the number of confirmed cases.

Preferably, the SUEIR model is:

$$R_n = R_{n-1} + \gamma IS_{n-1}$$
$$IS_n = IS_{n-1} - \gamma IS_{n-1} + \rho U_{n-1} + \lambda I_{n-1}$$
$$I_n = I_{n-1} + \varepsilon U_{n-1} - \lambda I_{n-1}$$
$$U_n = U_{n-1} - \rho U_{n-1} - \varepsilon U_{n-1} + \alpha U_{n-1}$$
$$E_n = E_{n-1} + \frac{r\beta I_{n-1} S_{n-1}}{N} - \alpha E_{n-1} + \frac{\sigma U_{n-1} S_{n-1}}{N} + \frac{IS_{n-1} S_{n-1}}{N}$$

wherein R is removed number, S is susceptible number, I is patient number, E is incubation number, U is unconfirmed morbidity number, IS is isolation number, $\gamma$ is removal rate, $\rho$ is associated isolation rate of unconfirmed persons, $\lambda$ is isolation rate of confirmed cases, $\alpha$ is morbidity rate, $\sigma$ is infection rate of unconfirmed persons, $\varepsilon$ is confirmed diagnosis rate, n is number of iterations, $\beta$ is infection rate of confirmed diagnosis, N is total number of people.

Preferably, a method for forecasting epidemic situation using the SUEIR model includes:
acquisition of historical data: acquiring a required data of confirmed cases;
parameter initialization: initializing all parameters to fitted values of a previous day by the SUEIR model;
state initialization: initializing all states of the SUEIR model to values of several days ago, and correcting the values according to a total number of real confirmed diagnoses of the day;
parameter fitting: deducing from an initial state to the day by the initialized parameters with the initialized state; and fine adjusting the parameters using a least square method according to a difference between true values of historical data and a result of the deduction; and
future epidemic forecasting: calculating a case data for a period of time in the future by the SUEIR model based on the fitted parameters and a state of the day.

Compared with the prior art, the disclosure has the following beneficial effects.

In the disclosure, firstly, the time sequence of the historical confirmed diagnosis data of a certain region is acquired, the approximate initial value of the parameter of the region is obtained by the SUEIR model, and then, the final parameters satisfying the historical confirmed diagnosis data is fitted using the least square method. At this time, the real parameters and the historical number of people in each state have been obtained, and the SUEIR model is used to calculate the number of people in each future state. Then, the number of confirmed cases is accumulated to forecast the confirmed number of the epidemic situation, that is, the effect of forecasting confirmed number is achieved.

BRIEF DESCRIPTION OF THE DRAWINGS

In order to explain the embodiments of the present disclosure or the technical solutions in the prior art more clearly, the following drawings that need to be used in the description of the embodiments or the prior art will be briefly introduced. Obviously, the drawings in the following description are only embodiments of the present disclosure. For those of ordinary skill in the art, other drawings can be obtained based on the drawings disclosed without creative work.

FIG. 1 is a diagram of the transition of illness state in the present disclosure.

DETAILED DESCRIPTION OF EMBODIMENTS

Technical solutions of the present disclosure will be clearly and completely described below with reference to the embodiments. Obviously, the described embodiments are only part of the embodiments of the present disclosure, not all of them. Other embodiments made by those skilled in the art without sparing any creative effort should fall within the scope of the disclosure.

Referring to FIG. 1, the present disclosure provides an epidemic forecasting model for policies of prevention, control and isolation, including:

establishing a SUEIR model;

dividing, by the SUEIR model, population according to an ability of infection and a way of infection;

classifying patients further into three states: unconfirmed, confirmed but not in isolation, and confirmed and in isolation;

calculating a number of people in each state in the future by using the SUEIR model; and accumulating the number of people in the confirmed state to realize the forecasting of the number of confirmed cases.

The SUEIR model classifies patients into three states: unconfirmed, confirmed but not in isolation, and confirmed and in isolation. Three state transformation paths, that is, from unconfirmed morbidity to isolation, from unconfirmed morbidity to confirmed, and from confirmed to isolation, are added. In addition, the three kinds of patients have different infection rates to susceptible populations.

The SUEIR model is:

$$R_n = R_{n-1} + \gamma I S_{n-1}$$

$$IS_n = IS_{n-1} - \gamma IS_{n-1} + \rho U_{n-1} + \lambda I_{n-1}$$

$$I_n = I_{n-1} + \varepsilon U_{n-1} - \lambda I_{n-1}$$

$$U_n = U_{n-1} - \rho U_{n-1} - \varepsilon U_{n-1} + \alpha U_{n-1}$$

$$E_n = E_{n-1} + \frac{\beta I_{n-1} S_{n-1}}{N} - \alpha E_{n-1} + \frac{\sigma U_{n-1} S_{n-1}}{N} + \frac{IS_{n-1} S_{n-1}}{N}$$

wherein R is removed number, S is susceptible number, I is patient number, E is incubation number, U is unconfirmed morbidity number, IS is isolation number, $\gamma$ is removal rate, $\rho$ is associated isolation rate of unconfirmed persons, $\lambda$ is isolation rate of confirmed cases, $\alpha$ is morbidity rate, $\sigma$ is infection rate of unconfirmed persons, $\varepsilon$ is confirmed diagnosis rate, n is number of iterations, $\beta$ is infection rate of confirmed diagnosis, N is total number of people. The infection rate of different patients is expressed by different parameters ($\beta$, $\sigma$), and the infection rate of isolated patients is 0. In practical application, it is approximately considered that $S_n = S_{n-1}$, because the ratio of the number of patients to the total population is usually less than 1%.

The method for forecasting epidemic situation using the SUEIR model includes the following steps.

Acquisition of historical data: a required data of confirmed cases is acquired. Specifically, the time series of confirmed diagnosis in different regions are obtained from public data platforms (such as Johns Hopkins University, Dingxiangyuan, WHO official website, etc.).

Parameter initialization: all parameters to fitted values of a previous day are initialized by the SUEIR model. If it's the first day to forecast the country, it is estimated based on the news reports. For example, if it is known from the news that the strict degree of isolation of close contacts in country A is higher than that in country B, but lower than that in country C, the associated isolation rate of unconfirmed persons in country B is 0.6, and that in country C is 0.9, then the associated isolation rate of unconfirmed persons in country A can be initialized as 0.7-0.8.

State initialization: all states of the SUEIR model to values of several days (usually 5-14 days) ago are initialized, and the values are corrected according to a total number of real confirmed diagnoses of the day (Correcting method: the number of isolated cases and the number of confirmed cases are corrected to the total number of confirmed cases, and the more or less cases are classified as unconfirmed persons). If it is the first forecast, the total number of confirmed cases will be allocated to the number of isolated cases and the number of confirmed cases according to the isolation rate of the country. The number of unconfirmed persons will be compared with other countries in the same stage (initial outbreak, accelerated outbreak, mitigation, etc.). The susceptible group is the total population of the country.

Parameter fitting: the state of the day is deduced from an initial state by the initialized parameters with the initialized state, and the parameters are fine adjusted using a least square method according to a difference between true values of historical data and a result of the deduction.

Future epidemic forecasting: a case data for a period of time in the future is calculated by the SUEIR model based on the fitted parameters and a state of the day. By adding the number of isolated cases and the number of confirmed cases at a certain time in the future, the forecast results of the number of confirmed cases of the day can be obtained.

In the disclosure, firstly, the time sequence of the historical confirmed diagnosis data of a certain region is acquired, the approximate initial value of the parameter of the region is obtained by the SUEIR model. For example, the initial infection rate of undiagnosed persons directly reflecting the popularity rate of masks is initialed as 0.1 in the United States and 0.03 in South Korea. Then, the final parameters satisfying the historical confirmed diagnosis data is fitted using the least square method. At this time, the real parameters and the historical number of people in each state have been obtained, and the SUEIR model is used to calculate the number of people in each future state. Then, the number of confirmed cases is accumulated to forecast the confirmed number of the epidemic situation, that is, the effect of forecasting confirmed number is achieved. The disclosure is suitable for large-scale infectious disease forecasting and impact analysis of policies of prevention and control in the information age. In addition to forecasting the number of confirmed cases, the disclosure can also model and explain the effect of the isolation policy in a certain area through parameters. For example, the parameter "isolation rate", which is transformed from the confirmed but not in isolation to the confirmed and in isolation, reflects the level of "all those in need are hospitalized" in a region. If all patients in an area are isolated immediately after diagnosis, then this parameter is far greater than 1 and approaches infinity.

Most of the parameters in this part are new to SUEIR, and each parameter corresponds to the effect of a kind of policies for prevention and control. In addition to the popularity rate of masks—infection rate of unconfirmed persons mentioned above, there are nucleic acid detection ability—confirmed diagnosis rate, secret screening strength—associated isolation rate of unconfirmed persons, and the degree of "all those in need are hospitalized"—isolation rate. After the initial values of these parameters are obtained through the news, the daily model and historical data are used for fitting. The relative level of parameters in different regions evaluates the effect of corresponding policies in different regions. For example, if the infection rate of unconfirmed persons in country A is higher than that in country B, the popularity rate of masks in country A is lower than that in country B.

Each embodiment in this specification is described in a progressive manner, and each embodiment focuses on the differences from other embodiments. The same and similar parts of each embodiment can be referred to each other. For the device disclosed by the embodiment, the description is relatively simple because it corresponds to the method disclosed by the embodiment. For the relevant points, please refer to the description of the method section.

The above description of the disclosed embodiments enables those skilled in the art to realize or use the present disclosure. Many modifications to these embodiments will be apparent to those skilled in the art. The general principle defined herein can be realized in other embodiments without departing from the spirit or scope of the present invention. Therefore, the present disclosure will not be limited to these embodiments shown herein, but will conform to the widest scope consistent with the principle and novel features disclosed herein.

What is claimed is:

1. A method for forecasting epidemic situation based on a susceptible-exposed-infectious-recovered (SUEIR) model for policies of prevention, control and isolation, comprising:
    establishing the SUEIR model;
    dividing, by the SUEIR model, population according to an ability of infection and a way of infection;
    classifying patients into three states: unconfirmed, confirmed but not in isolation, and confirmed and in isolation;
    calculating a number of people in each state in the future by using the SUEIR model and
    accumulating the number of people in the confirmed state to realize the forecasting of the number of confirmed cases;
    wherein the SUEIR model comprises:

$$R_n = R_{n-1} + \gamma IS_{n-1}$$

$$IS_n = IS_{n-1} - \gamma IS_{n-1} + \rho U_{n-1} + \lambda I_{n-1}$$

$$I_n = I_{n-1} + \varepsilon U_{n-1} - \lambda I_{n-1}$$

$$U_n = U_{n-1} - \rho U_{n-1} - \varepsilon U_{n-1} + \alpha U_{n-1}$$

$$E_n = E_{n-1} + \frac{\beta I_{n-1} S_{n-1}}{N} - \alpha E_{n-1} + \frac{r\sigma U_{n-1} S_{n-1}}{N} + \frac{0 * rIS_{n-1} S_{n-1}}{N}$$

wherein R is removed number, S is susceptible number, I is patient number, E is incubation number, U is unconfirmed morbidity number, IS is isolation number, $\gamma$ is removal rate, $\rho$ is associated isolation rate of unconfirmed persons, $\lambda$ is isolation rate of confirmed cases, $\alpha$ is morbidity rate, $\sigma$ is infection rate of unconfirmed persons, $\varepsilon$ is confirmed diagnosis rate, n is number of iterations, $\beta$ is infection rate of confirmed diagnosis, N is total number of people;

wherein the method for forecasting epidemic situation using the SUEIR model further comprises:
acquisition of historical data: acquiring a required data of confirmed cases in different regions;
parameter initialization: initializing all parameters to fitted values of a previous day by the SUEIR model;
state initialization: initializing all states of the SUEIR model to values of several days ago, and correcting the values according to a total number of real confirmed diagnoses of the day;
parameter fitting: deducing from an initial state to the day by the initialized parameters with the initialized state; and fine adjusting the parameters using a least square method according to a difference between true values of historical data and a result of the deduction; and
future epidemic forecasting: calculating a case data for a period of time in the future by the SUEIR model based on the fitted parameters and a state of the day to provide relative level of parameters in different regions and further evaluation of effect of corresponding policies in different regions.

* * * * *